(12) United States Patent
Alexander et al.

(10) Patent No.: US 7,575,780 B2
(45) Date of Patent: *Aug. 18, 2009

(54) METHOD FOR MANUFACTURING PARTICLES FOR USE IN FORMING A RESORBABLE IMPLANT FOR STIMULATING BONE GROWTH

(75) Inventors: Harold Alexander, Short Hills, NJ (US); John L. Ricci, Middleton, NJ (US); Sachin Mamidwar, Edison, NJ (US)

(73) Assignee: Orthogen LLC, Springfield, NJ (US)

( * ) Notice: Subject to any disclaimer, the term of this patent is extended or adjusted under 35 U.S.C. 154(b) by 331 days.

This patent is subject to a terminal disclaimer.

(21) Appl. No.: 11/369,322

(22) Filed: Mar. 6, 2006

(65) Prior Publication Data

US 2006/0204586 A1 Sep. 14, 2006

Related U.S. Application Data

(63) Continuation-in-part of application No. 10/892,509, filed on Jul. 14, 2004, now Pat. No. 7,488,761, which is a continuation-in-part of application No. 09/918,445, filed on Aug. 1, 2001, now Pat. No. 6,770,695.

(60) Provisional application No. 60/223,624, filed on Aug. 7, 2000.

(51) Int. Cl.
*B01F 3/12* (2006.01)
*C08K 9/10* (2006.01)
*B01J 13/00* (2006.01)

(52) U.S. Cl. ............... 427/226; 427/219; 523/115; 523/205; 523/322

(58) Field of Classification Search .......... 523/322, 523/115, 205; 427/226
See application file for complete search history.

(56) References Cited

U.S. PATENT DOCUMENTS

| | | | | |
|---|---|---|---|---|
| 2,701,767 | A | * | 2/1955 | Twieg et al. ............. 426/97 |
| 3,753,767 | A | * | 8/1973 | Becker ............... 427/2.2 |
| 5,085,861 | A | | 2/1992 | Gerhart et al. |
| 5,681,873 | A | | 10/1997 | Norton et al. |
| 5,747,390 | A | | 5/1998 | Cooper et al. |
| 5,958,961 | A | * | 9/1999 | Inada et al. ............. 514/394 |
| 6,048,521 | A | | 4/2000 | Kohn et al. |
| 6,224,635 | B1 | | 5/2001 | Ricci et al. |
| 6,613,360 | B1 | * | 9/2003 | Maa ................... 424/490 |
| 2002/0110541 | A1 | | 8/2002 | Petersen |
| 2008/0233165 | A1 | * | 9/2008 | Alexander et al. ....... 424/423 |

* cited by examiner

*Primary Examiner*—Tae H Yoon
(74) *Attorney, Agent, or Firm*—Melvin K. Silverman; Yi Li

(57) ABSTRACT

A bone-growth stimulating composition for forming a resorbable implant, methods for making such a composition and a corresponding putty/paste material. In some embodiments of the invention, such a material includes a plurality of particles having a predetermined size and comprising a first calcium sulfate compound and a resorbable polymer in a predetermined weight ratio. Methods for making such a material include rotating calcium sulfate powder in a drum at a first predetermined drum speed, spraying of a resorbable polymer solution at a predetermined rate on the calcium sulfate powder over a predetermined period of time and drying the resulting particles. Such compositions allow resorption rates of the implant composition in vivo to be controlled, and my vary between eight and twenty-four weeks (for example), which can be matched to substantially correspond to a rate of bone growth in a particular application. The implant composition of the present invention can be used for the repair, augmentation, and other treatment of bone.

53 Claims, 12 Drawing Sheets

FIG. 10A
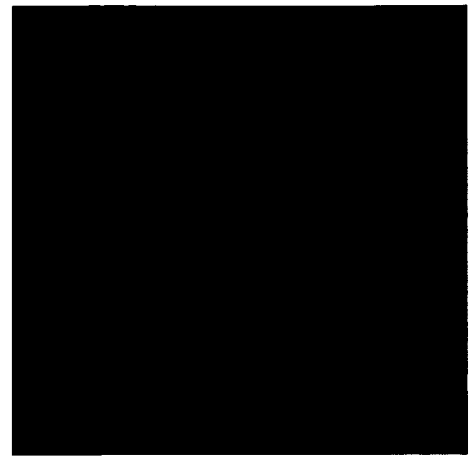
FIG. 10B
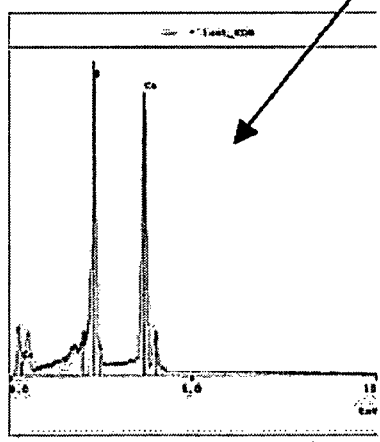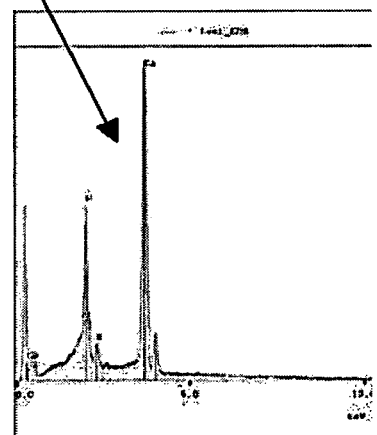
FIG. 11

Bone observed in the areas just outside of the BoneGen–TR implant

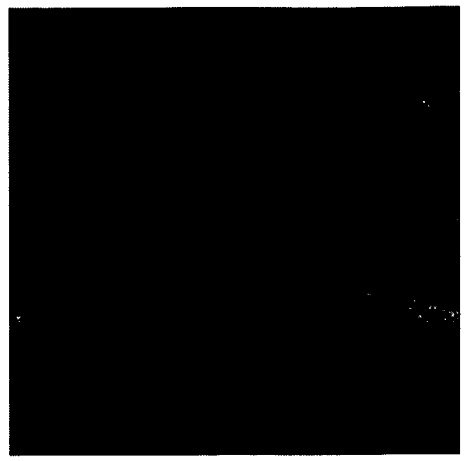
FIG. 13B
 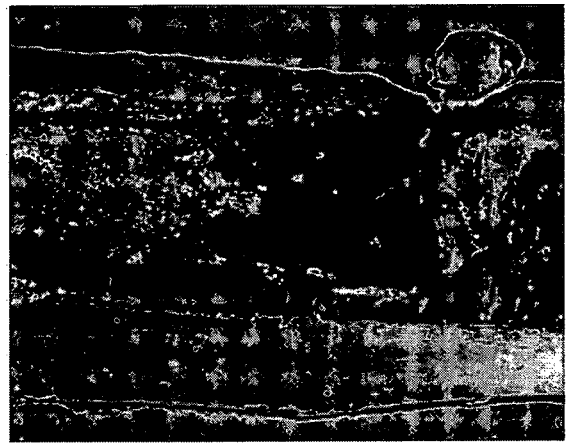
FIG. 14A                    FIG. 14B

METHOD FOR MANUFACTURING PARTICLES FOR USE IN FORMING A RESORBABLE IMPLANT FOR STIMULATING BONE GROWTH

REFERENCE TO RELATED APPLICATION

This application is a continuation-in-part to U.S. application Ser. No. 10/892,509, filed Jul. 14, 2004, now U.S. Pat. No. 7,488,761, issued Feb. 10, 2009, which is a continuation-in-part of U.S. application Ser. No. 09/918,445, filed Aug. 1, 2001, now U.S. Pat. No. 6,770,695, issued Aug. 3, 2004, which claims priority to U.S. provisional patent application No. 60/223,624, filed Aug. 7, 2000. Each of the foregoing references is herein incorporated by reference in their entirety.

BACKGROUND OF THE INVENTION

The repair of bone defects and augmentation of existing bone often require the use of permanent bio-resorbable materials. Such materials may include autogenous bone graft, allogeneic graft, allogeneic bone graft, or alloplastic materials inclusive of various calcium phosphate ceramics, calcium phosphate cements, calcium sulfate materials, bioglass materials, and composites or other combinations thereof. Calcium sulfate, which is a form of plaster of paris, is a fully bioresorbable material which, for sometime, has been commonly used in cement and pellet form to repair bone defects.

When calcium sulfate is used as a cement to fill a bone void, fracture, or other defect, this material dissolves at a rapid rate, i.e., approximately one millimeter per week from the exterior of the cement towards the center thereof. Research of the present inventors has shown that this material causes precipitation of calcium phosphate deposits as it is resorbed at the surgical site. These precipitates, it has been shown, stimulate and direct the formation of new bone. On the other hand, it is important for purposes of optimal result that calcium sulfate, calcium phosphate, or any other bone repair material stay at the surgical site for a considerable period of time in order to inhibit soft tissue filling of the defect and to stimulate bone repair. However, currently used calcium sulfate materials are typically resorbed by human bone within two to seven weeks, depending upon the calcium sulfate form and the particular surgical site, which cannot be retained at the site for longer periods. As noted, such material is resorbed faster than it can be replaced by new bone thereby reducing its value to both patient and practitioner.

As such, the principal concern and difficulty expressed by practitioners (such as orthopedics or maxiofacial surgeons) are that calcium sulfate materials bio-resorb or dissolve too rapidly at a surgical or a recipient site, and, thereby, outpace the formation of new bone in human patients. Therefore, a need arises for improved calcium sulfate based compositions which can resorb at the recipient site in a rate desirably matching the rate bone growth.

SUMMARY OF THE INVENTION

The present invention relates to an implant composition having controlled resorption rate in vivo for stimulating bone growth, a particle used in such a composition, methods of making such implant compositions, and a calcium sulfate putty/paste.

In one aspect of the present invention, an implant composition having controlled resorption rate comprises a calcium sulfate compound, polymer containing particles, and a setting agent for setting the calcium sulfate compound and the polymer containing particles into a heterogeneous solid composition. Upon setting, the calcium sulfate compound forms a matrix and the polymer containing particles settled within the matrix.

In another aspect, the present invention comprises a method of using implant materials to make the inventive implant composition for bone augmentation and bone defect reparation. The method comprises the steps of: (a) mixing a calcium sulfate compound and polymer containing particles with a setting agent into a mixture, (b) applying the mixture, either by filling in a recipient site with the mixture, or by coating the mixture on a surface of a surgical implant prior to introducing the surgical implant into the recipient site, and (c) setting the mixture into a heterogeneous solid composition.

In a further aspect, the present invention relates to a kit of implant materials for bone augmentation and bone defect reparation. The kit comprises (a) dry powder of a calcium sulfate compound, and (b) polymer containing particles. The kit can further comprise a setting agent packed in a container, and instructions on how to use the kit for preparing the implant composition.

In another aspect of the present invention, a bone-growth stimulating particle is presented, a plurality of which for use together for forming a resorbable implant. The particle includes a size between about 425-850 μm in diameter and comprises a calcium sulfate compound and a resorbable polymer in a weight ratio of about 96:4 (for example).

In yet another aspect of the present invention, a bone-growth stimulating composition for forming a resorbable implant includes a plurality of particles having a size between about 425-850 μm in diameter and including a first calcium sulfate compound and a resorbable polymer in a weight ratio of about 96:4.

In yet another aspect of the invention, a bone-growth stimulating putty/paste for forming a resorbable implant is provided and comprises calcium sulfate powder, a plurality of polymer containing particles and a plasticizer/thickener. Such plasticizers/thickeners include at least one of, for example, carboxymethylcellulose, hydroxymethylcellulose, hydroxyethylcellulose, hydroxypropyl methylcellulose, hydroxyethylcellulose polyvinyl alcohol, polyvinyl pyrrolidone, hyaluronate and chitin derivatives such as chitosan.

The polymer containing particles in some embodiments of the putty may include a weight ratio of calcium sulfate to resorbable polymer of about 96:4 (or other weight ratio as presented in other embodiments of the present disclosure. In addition, a weight ratio of the polymer containing particles to the plasticizer/thickener may be between about 65:35 to 90:10.

Some of the putty material embodiments may also include, in addition to the polymer containing particles and plasticizer/thickener, a calcium sulfate powder, and a weight ratio of polymer containing particles to calcium sulfate to the plasticizer/thickener may be between about 60:30:10 to about 75:15:10.

In yet another aspect of the invention, a method for manufacturing particles for use in forming a resorbable implant for stimulating bone growth is provided and includes rotating calcium sulfate powder in a drum at a first predetermined drum speed, a first spraying of a resorbable polymer solution at a first predetermined rate on the calcium sulfate powder over a first predetermined period of time and drying the resulting particles.

It is accordingly an object of some of the embodiments of the present invention to provide an implant composition for the repair and augmentation of bone defects.

It is another object of some of the embodiments of the invention to provide an implant composition having controllable resorption rate in vivo, wherein the rate of resorption can be substantially matched to the rate of bone growth in a specific medical or dental application.

It is a further object of some of the embodiments of the invention to provide implant materials and a method for making the implant composition.

The above and yet other objects and advantages of the present invention will become apparent from the hereinafter set forth Brief Description of the Drawings and Detailed Description of the Invention.

BRIEF DESCRIPTION OF THE DRAWINGS

FIG. 10A is an image of a bone having an implant composition material according to one embodiment of the present invention, four weeks after implantation.

FIG. 10B is an image of a bone having an implant composition material comprising pure calcium sulfate four weeks after implantation.

FIG. 11 is an enlarged image of a bone having an implant composition material according to one embodiment of the present invention, four weeks after implantation, with corresponding SRM graphs, illustrating that both calcium sulfate and calcium phosphate are present.

FIG. 13B is an image of an implant composition material comprising pure calcium sulfate implant eight weeks after implantation, illustrating that most of the original calcium sulfate has been degraded with very little bone growth.

FIG. 14A is an image illustrating the histological response of a bone having an implant composition material according to one embodiment of the present invention at eight weeks after implantation.

FIG. 14B is an image illustrating the histological response of a bone having an implant composition material comprising pure calcium sulfate at eight weeks after implantation.

DETAILED DESCRIPTION OF THE INVENTION

Figure 1:
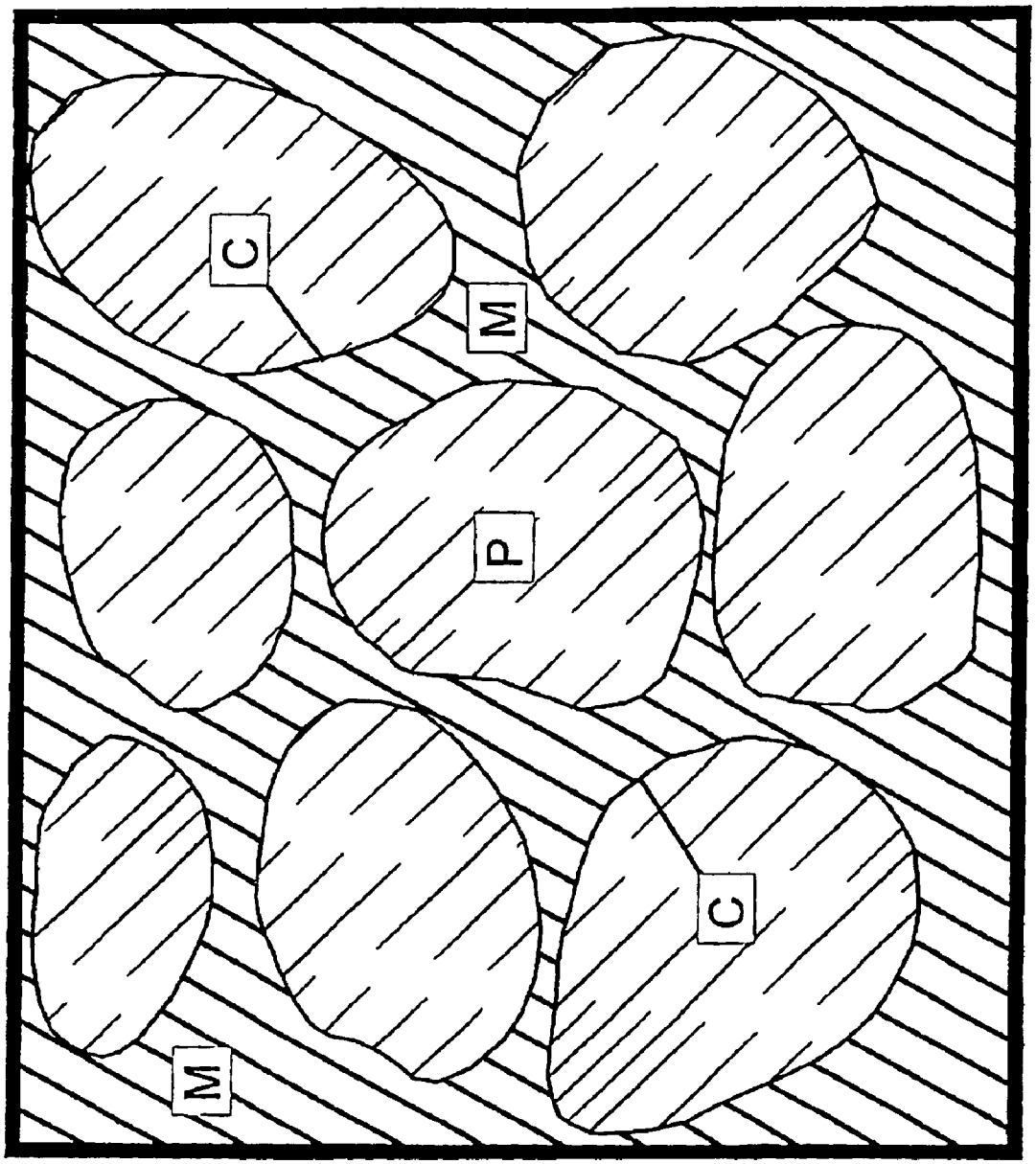
FIG. 1 is a schematic view of an implant composition of one embodiment of the present invention immediately after introduction into a recipient site, showing the heterogeneous solid implant composition.

In one aspect of the present invention, an implant composition having controlled resorption rate comprises a calcium sulfate compound, polymer containing particles, and a setting agent for setting the calcium sulfate compound and the polymer containing particles into a heterogeneous solid composition. Upon setting, the calcium sulfate compound forms a matrix (M) and the polymer containing particles (P) settled within the matrix. FIG. 1 shows a cross-sectional schematic view of the heterogeneous solid implant composition before resorption occurs.

In another aspect, the present invention comprises a method of using implant materials to make the inventive implant composition for bone augmentation and bone defect reparation. The method comprises the steps of: (a) mixing a calcium sulfate compound and polymer containing particles with a setting agent into a mixture, (b) filing a recipient site with the mixture, and (c) setting the mixture into a heterogeneous solid composition.

The calcium sulfate compound preferably is a dry powder of preferably calcium sulfate hemihydrate, having a particle size between about sub-micron to about 20 microns. Suitable setting agents include water, alkaline metal salt solutions such as a saline solution, and an accelerant aqueous solution containing potassium salt. The setting agents set the implant materials into a heterogeneous solid composition, or a multiphasic cement with different speeds. The speed of setting can be controlled from seven minutes to one hour, depending on the setting agent used as well as desired surgical application. Among various setting agents, potassium salt solutions result in the fastest setting. For the purpose of the present invention, an aqueous solution containing potassium or sodium ions are preferably used. Most preferably, an aqueous solution containing potassium ions can be used. Suitable examples of potassium salts include potassium sulfate, potassium phosphate, and potassium fluoride. The concentration of potassium ion controls the speed of setting, the higher it is the faster the setting process. Preferably, the concentration of the potassium ions is in a range from about 0.01 molar to about 0.5 molar.

The polymer containing particles (P) comprises a calcium sulfate compound, and at least one resorbable polymer. The calcium sulfate compound in the polymer containing particles can be calcium sulfate dihydrate, also called preset calcium sulfate, or calcium sulfate hemihydrate, also called unset calcium sulfate, or a mixture thereof. In one embodiment, the calcium sulfate compound is mixed with a resorbable polymer to form the particles. The amount of resorbable polymer used in the particles controls resorption rate of the implant composition when it is implanted in a recipient site. In an alternative embodiment, the calcium sulfate compound of the particles is encapsulated in a coating (C) of a resorbable polymer, as shown in FIG. 1. In this case, thickness of the resorbable polymer coating controls resorption rate of the implant composition in a recipient site. The thickness of the resorbable polymer coating is from about 2 microns to about 50 microns. For polymers that are only expected to last for a short time, a thin layer can be applied. For fast-resorbing coatings, or coatings expected to last for a long time, a thick coating can be applied. Furthermore, the resorbable polymer coating is not required to be a complete encapsulation. It has been observed that small local incomplete coatings, or coatings with defects (accidentally or intentionally), function as initial resorption sites of the polymer containing particles. An analogous situation can be found in time release medicine. It is known that medical pills with small controlled defects (drilled or molded) in polymer coatings are sometimes used to control drug release rates. A broad range of particle sizes can be used in the implant composition. The particle size can be determined depended on a particular application, and recipient site. For example, small particles are more suitable for dental fillings. On the other hand, larger pallets are more suitable for repairing bone fracture. Preferably, the particle size is more than 20 microns in diameter since when the particles are smaller than 20 microns, they may cause a negative foreign body response due to activation of macrophages.

In an additional embodiment, the particles can be made having combined characteristics of the two types of particles described above. Herein, the particles can include mixed calcium sulfate compound and a resorbable polymer, which are, additionally, encapsulated with a resorbable polymer coating.

In a further embodiment, the implant composition comprises two different types of polymer containing particles that have different rates of resorption. Such particles can, for example, be particles coated with different polymers, combinations of coated and mixed polymers, or particles with coating of different thickness, a typical range being 0.5 to 100 micrometers.

A wide variety of resorbable polymers can be used for the implant composition of the present invention. Suitable resorbable polymers include aliphatic polyesters of alpha-hydroxy acid derivatives, such as polylactides, polyglycolides, polydioxanone, and poly ε-caprolactone; hydrophobic polymers, such as carnuba waxes and their derivatives; water soluble polymers, such as poly(desaminotyrosyl-tyrosine ethyl ester carbonate), hereinafter poly (DTE carbonate) and their derivatives; and therapeutic polymers, such as those containing salicylate. A specific type of resorbable polymer can be selected depending on the purpose of applications, expected bone growth speed of a particular surgical site, and environment or condition of a recipient site. For the purpose of the present invention, polylactides, polyglycolides and poly (DTE carbonate) are used preferably. It is known that polylactides, including D and L isomers, and DL copolymers of polylactic acid, have a long time history in their use as biomedical devices. These polymers are readily available commercially. The polyglycolides and poly (DTE carbonate) have also been used for bone reparation.

In general, resorbable polymers resorb slower in vivo than calcium sulfate compounds. Therefore, the amount of resorbable polymer used in the particles, mixed or coated, controls resorption rate of the implant composition when it is implanted in a recipient site. The polymer containing particles can comprise about 0.1% to about 50% (w/w) of a resorbable polymer, with about 1.5% defining the best mode. When the amount of a resorbable polymer is too high, it may cause a negative body, that is, immune response. When used as a coating only, the above (w/w) range is about 0.1% to about 22%. The rate of resorption of the implant composition can be controlled of between three (3) and twenty eight (28) weeks (for example), depending on the types and amount of polymer(s) used.

In an additional embodiment, the present invention relates to a method of preparing the polymer containing particles. The polymer containing particles can be prepared by two methods: (1) a surface coating process, and (2) bulk mixing of polymer and calcium sulfate. In the surface coating process, preformed calcium sulfate particles are mixed with a polymer solution. The polymer solution forms a liquid coating on the calcium sulfate particles, and is allowed to dry and to form a polymer surface coating on the particles. The coating thickness and amount of penetration into the calcium sulfate depend on the concentration of polymer in the solution, and viscosity of the solution. Examples of suitable organic solvent can be used to dissolve the polymer and make the polymer solution include acetone and chloroform. In the bulk mixing method, a fine granular form of a polymer is mixed with a granular form of calcium sulfate. The mixture is then pressed or rolled into larger particles.

In another embodiment of the present invention, the polymer containing particles may be made as follows. A dilute L-polylactide (PPLA) solution is prepared by dissolving PLLA in methylene chloride (or other similar solvent). The PLLA solution may then be sprayed on calcium sulfate powder (e.g., calcium sulfate hemihydrate) in a rotating drum machine (e.g., Freund GX-20 Granurex). The mixture may then be rotated until small pellets are formed. The pellets may then be air dried for several hours, and then may be sieved. Pellets of between 425 to 850 microns are produced, and preferably, particles sized between about 425 to about 600 microns. A preferred weight ratio of calcium sulfate to PLLA (by weight) is between about 83:17 to about 97:3, with a most preferred weight ratio of about 96:4.

Specifically, polymer containing particles of a size outlined above may be made as follows. First, the rotating drum mechanism is preheated to between about 40° C. and 80° C., and preferably about 50° C. Calcium sulfate hemihydrate powder is added to the drum and the drum is then rotated between about 200 and 400 RPM, and preferably at about 350 RPM (either prior to, during or after addition of the calcium sulfate). A PLLA solution is sprayed onto the calcium sulfate powder at approximately 60 grams per minute (±10 grams per minute) between about 10-20 minutes, and preferably for about 15 minutes. The drum speed is then increased 10-20%, or between about 300 to about 500, and preferably to about 400 RPM, and the PLLA solution is then sprayed onto the calcium sulfate/PPLA solution mixture at a rate of about 40 grams per minute (±10 grams per minute) for between about 100-300 minutes, and preferably about 200 minutes. Formed particles are then air dried in the drum and rotor speed is decreased between about 25-50%, or between about 200-300 RPM, and preferably to about 250 RPM (generally between about 50-80 minutes, and preferably for about 60 minutes). The dried particles are preferably substantially free of the solvent used in the PLLA solution. The particles may then be removed, and the drum mechanism cooled thereafter by rotating the drum at about 250 RPM for about 10 minutes or however much longer it takes to cool down the drum.

In one example of the above embodiment, a preferred weight ratio of calcium sulfate to polymer is about 96:4. For example, a PLLA solution of 30.6 grams of PLLA dissolved in about 7619.4 grams of methylene chloride (or other similar solvent) is sprayed onto 574.5 grams of calcium sulfate. In this example, only about 70-80% (and preferably about 77%) of the PLLA solution need be sprayed onto the calcium sulfate to obtain the weight ratio of about 96:4 calcium sulfate to PLLA (and, in one aspect, a most preferred weight ratio of about 95.75:4.25), which corresponds to about 77.2% of the PLLA. This weight ratio corresponds to a material which substantially, and more preferably, completely degrades in about 16 weeks in vivo (according to some embodiments of the invention).

Figure 8:
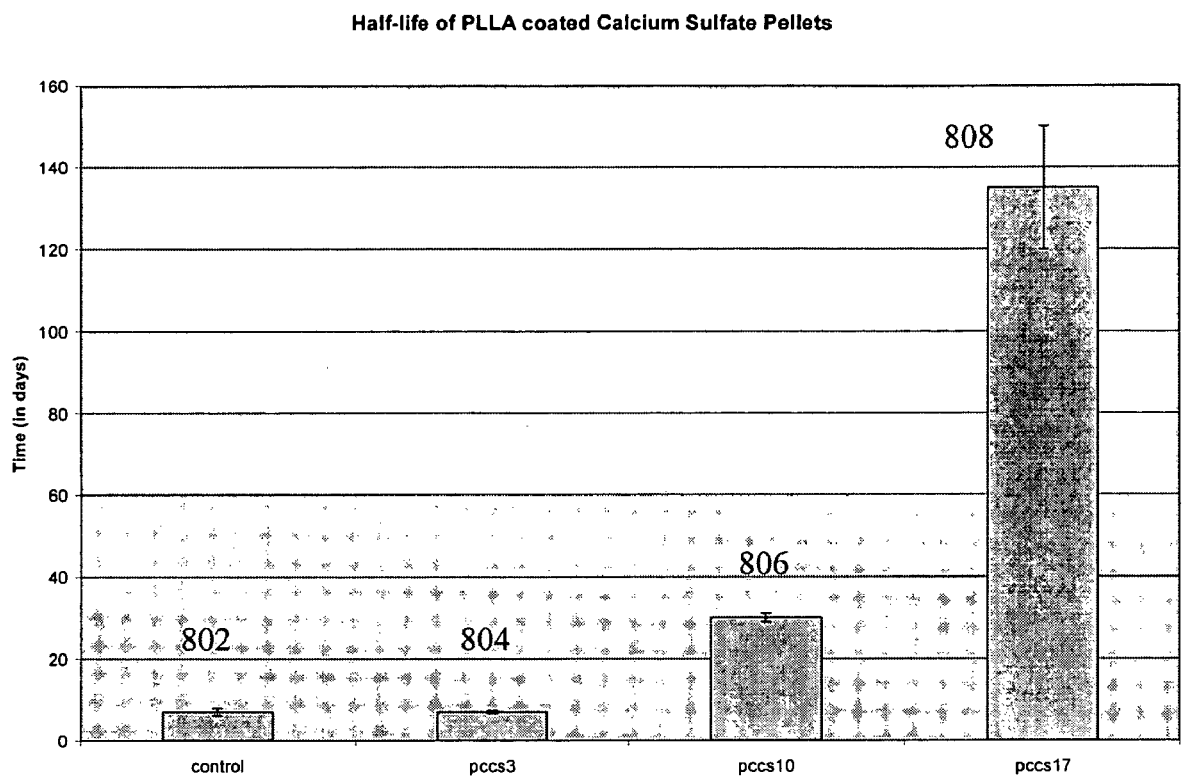
FIG. 8 is a graph illustrating the half-life of some of the implant composition materials according to some of the embodiments of the present invention.

FIG. 8 is a graph illustrating the half-life of pure calcium sulfate (802), polymer-containing particles corresponding to a calcium sulfate to PLLA weight ratio of 97:3 (804), polymer-containing particles corresponding to a calcium sulfate to PLLA weight ratio of 90:10 (806), and polymer-containing particles corresponding to a calcium sulfate to PLLA weight ratio of about 83:17 (808). Although not shown, a material having a calcium sulfate to PLLA weight ratio of about 96:4 includes a typical half-life of about 70 days, with only 10% of the material being left after 135 days (the 10% of material that is left will most likely be calcium phosphate). As can be seen, the 83:17 weight ratio polymer containing particles show considerable longer half-life over calcium sulfate or any of the other two weight ratio examples listed or pure calcium sulfate.

In still other embodiments, polymer containing particles may be made by first creating calcium sulfate particles of between about 700 to 1000 microns first and thereafter coating the particles. Such calcium sulfate particles may be created by making a calcium sulfate mixture, which may be made by mixing calcium sulfate with distilled (preferably) water in a weight ratio of about 1 gram of calcium sulfate to about three-tenths (0.3) grams of water. This mixture may then be pressed molded into 700-1000 microns (for example) and then dried. Such particles may then be coated with a PLLA/methylene chloride (solvent) solution (e.g., the solution listed above) and allowed to dry. The weight ratio of calcium sulfate to PLLA for such polymer containing particles may be between about 83:17 to about 97:3.

Some embodiments of the present invention are directed to a calcium sulfate putty having polymer containing particles. One such embodiment comprises a mixture of polymer containing calcium sulfate particles according to any of the embodiments noted in the present disclosure (e.g., calcium Sulfate(CS)/PLLA composite) and a plasticizer/thickener, in a weight ratio of CS/PLLA:plasticizer/thickener of between about 65:35 to 90:10, and preferably about 85:15. Such plasticizers/thickeners may include, for example, at least one of carboxymethylcellulose, hydroxymethylcellulose, hydroxyethylcellulose, hydroxypropyl methylcellulose, hydroxyethylcellulose polyvinyl alcohol, polyvinyl pyrrolidone, hyaluronate and chitin derivatives such as chitosan.

Another such embodiment may comprise the polymer containing calcium sulfate particles, a separate calcium sulfate powder and a plasticizer/thickener in a weight ratio of CS/PLLA:CS:plasticizer/thickener between about 60:30:10 to about 75:15:10, and preferably about 70:20:10. Such material may also be prepackaged for sale and use.

Figure 2:
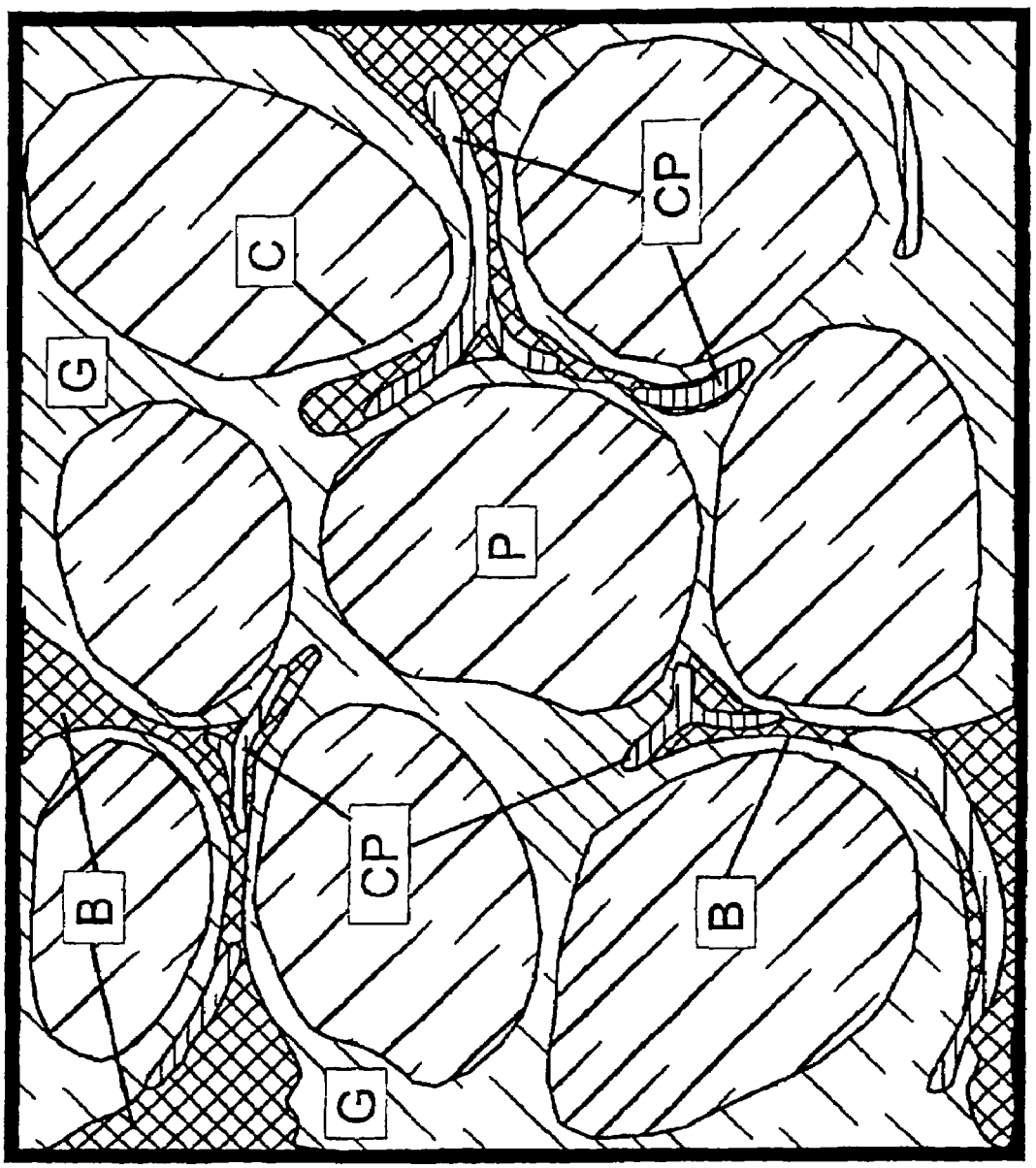
FIG. 2 is a view, sequential to that of FIG. 1, showing a first phase of bioresorption of the implant composition at the recipient site.

FIG. 1 to FIG. 4 illustrate the resorption process of the implant composition of the present invention, according to some embodiments of the invention, and the mechanism of controlled resorption rate for a proper stimulation of bone growth. FIG. 1 shows the structure of the heterogeneous solid implant composition after the mixture of calcium sulfate compound, polymer encapsulated particles, and the setting agent is being applied in a recipient site, and set into a heterogeneous solid composition. FIG. 2 shows the first phase of bioresorption of the implant composition. The calcium sulfate compound in the matrix resorbs first, that is, the first two to four weeks (generally) after implantation, thereby forming a porous system which will fill with granulation tissue (G) during said timeframe. The process of resorbing calcium sulfate forms deposits of calcium phosphate (CP) which has function to encourage early bone in-growth (B).

Figure 3:
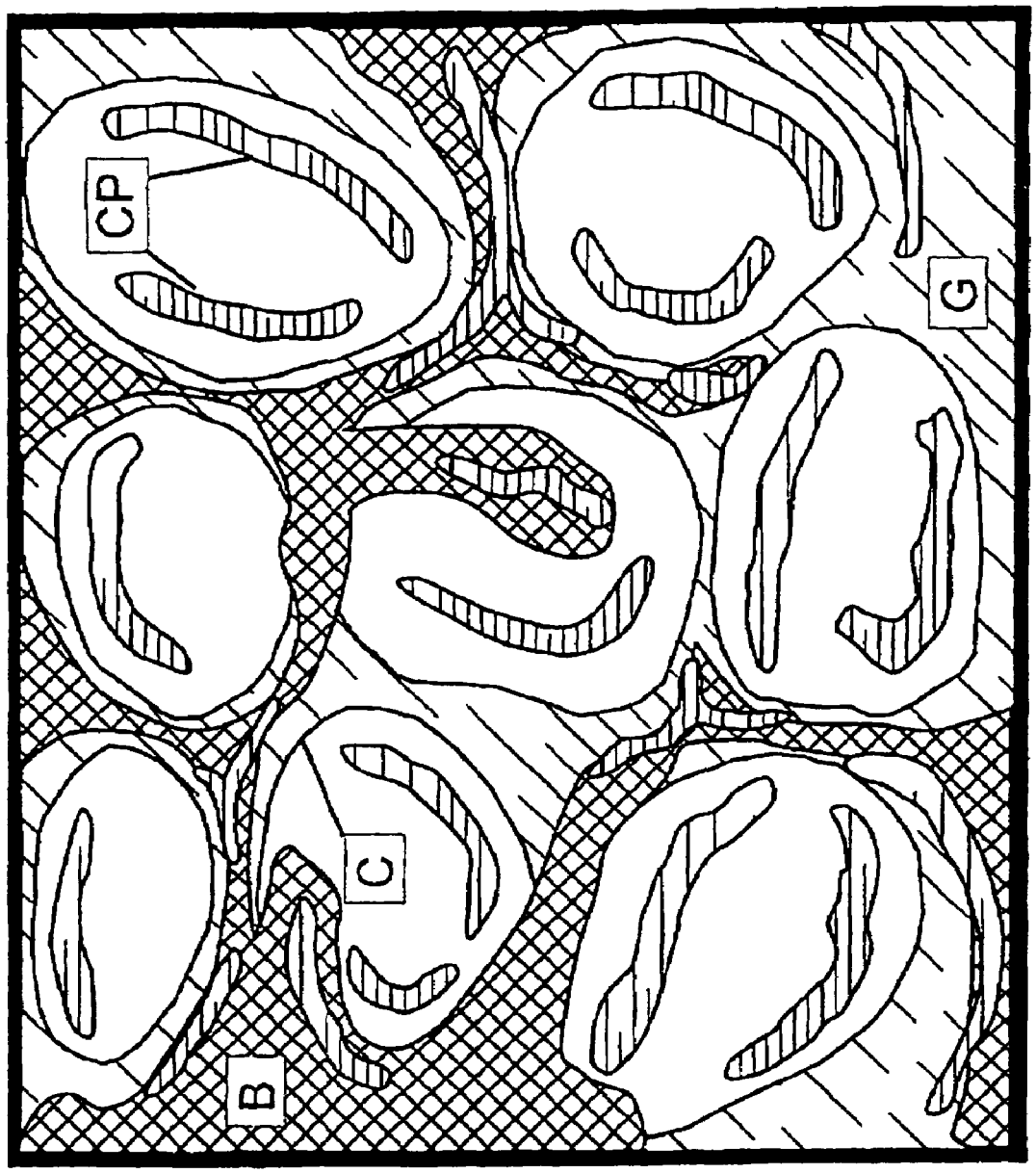
FIG. 3 is a view sequential to that of FIG. 2 showing the beginning of resorption of the polymer containing particles of the implant composition.

FIG. 3 shows the second phase of the resorption, i,e., resorption of the polymer containing particles. This generally occurs as early as four weeks or as late as twenty weeks after applying the implant composition, depending upon the particular formulation of the composition and application. In the example, as reflected in FIG. 3, the polymer coating has partially broken down allowing resorption of the encapsulated calcium sulfate compound. Therein, the resorbing calcium sulfate compound produces deposits of calcium phosphate (CP) as in the first phase of resorption (see FIG. 2), and additional bone in-growth will occur.

Figure 4:
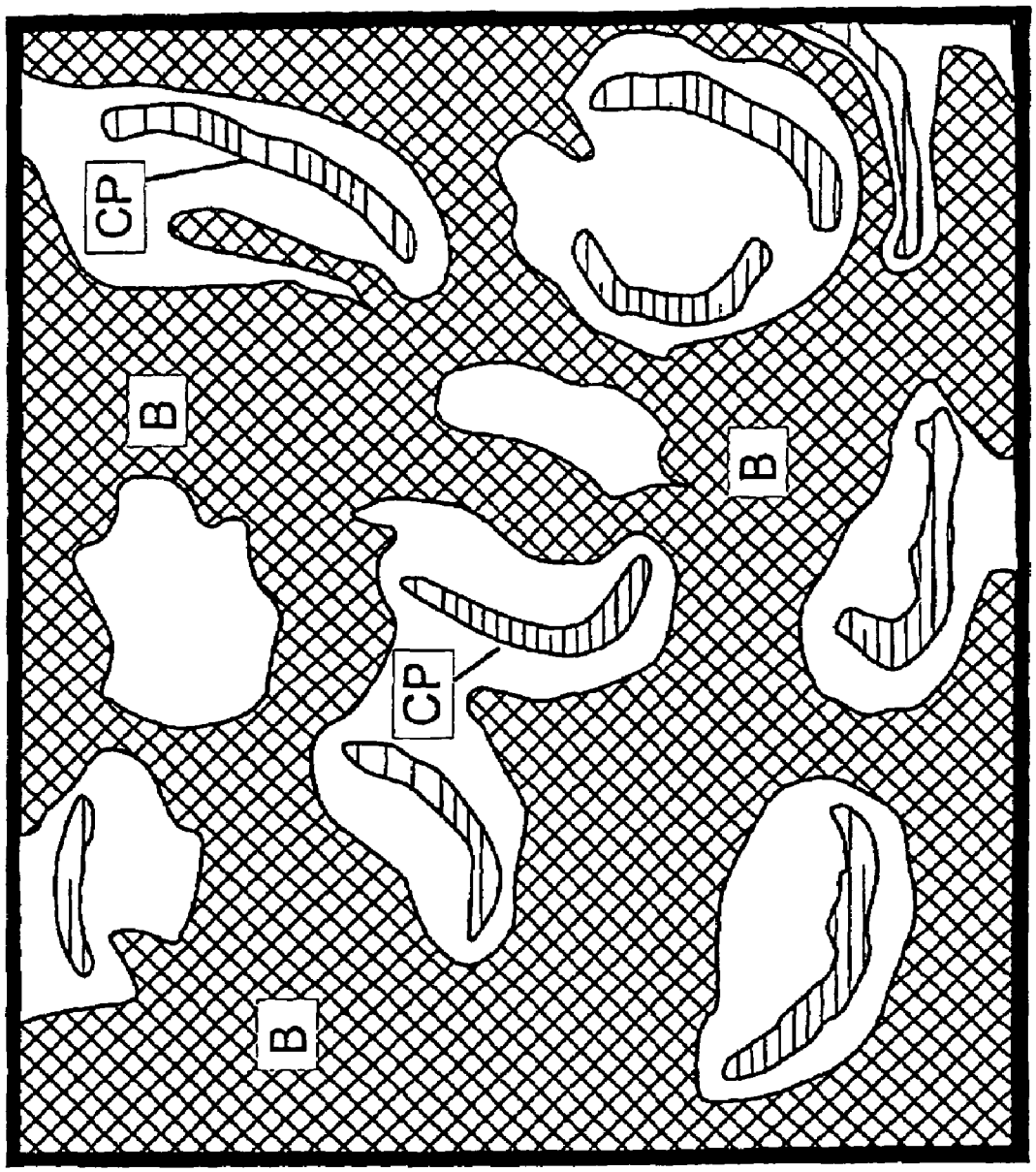
FIG. 4 is a view, sequential to that of FIG. 3, showing the end result of the bioresorption of the implant composition, which results stimulated bone growth with diminishing level of the implant composition.

FIG. 4 shows the end result of the resorption of the implant composition. This occurs generally as early as six weeks or as late as twenty four weeks depending upon the particular formulation of the composition and application (for example). By this time only residual amount of polymer material remains and full bone in-growth has occurred. In addition, most calcium phosphate deposits have been removed by bone remodeling, only a small amount of calcium phosphate deposits within the original particles can still be visible in new bone growth. It is understood that bone remodeling is a natural process that normally occurs very slowly. Remodeling occurs as new bone is constantly formed by osteoblasts and removed by osteoclasts. The balance of the two processes represents an equilibrium that determines how much bone is present at any given time. However, remodeling is rapid during healing, and virtually all of the immature bone that is formed during early healing is remodeled and replaced by more mature bone. The calcium phosphate deposits formed by the dissolving calcium sulfate are similar to bone mineral, and are also remodeled and replaced by more mature bone during this period of time.

The implant composition of the present invention can be used for the repair, augmentation, and other treatment of bone. The implant composition possesses significant advantages over existing calcium sulfate cements and pellets used clinically for bone repair and regeneration. More particularly, current calcium sulfate materials are typically resorbed by human bone within two to seven weeks, depending upon the calcium sulfate form and the particular surgical site, however, cannot be retained at the site for longer periods. As noted, such material is resorbed faster than it can be replaced by new bone thereby reducing its value to both patient and practitioner. The implant composition of the present invention can be designed to resorb in phases in accordance with the needs of a specific surgical application and environment of a recipient site, therein allowing substantial control of resorption rate. The resorption rate can be controlled, for example, between eight and twenty four weeks (for example), which substantially matches the rate of bone growth.

On the other hands, since methods involving separate use of calcium sulfate and polymeric components have long been established as safe and fully bioresorbable, clinical utilities and feasibility of the present invention are apparent. In particular, the implant composition of the present invention can be applied in dentistry for bone repairing and augmentation with or without a surgical implant.

Figure 5:
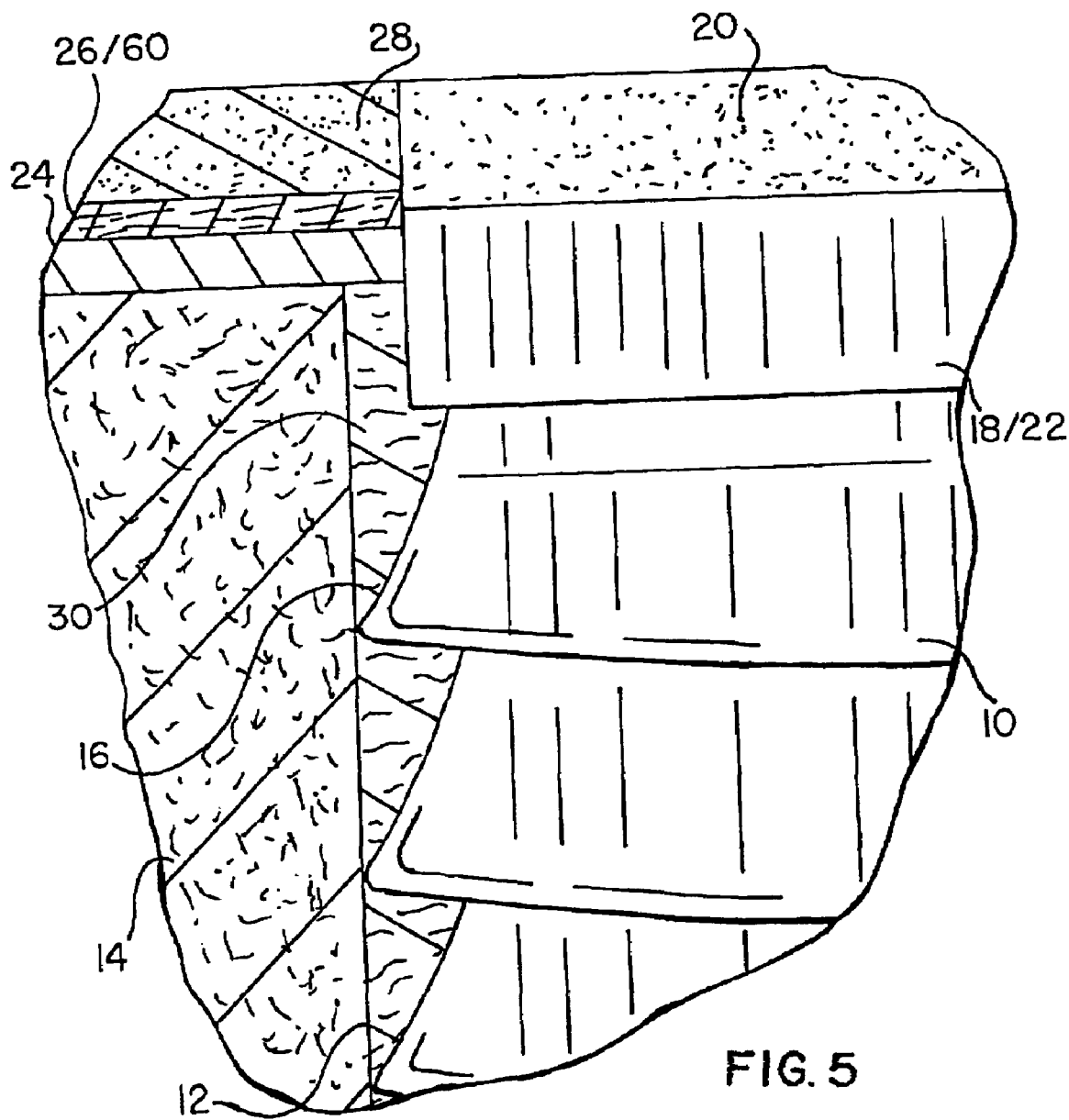
FIG. 5 is a cross-sectional schematic view of the implant composition of the present invention used with a surgical implant which has buttress threads.
Figure 7:
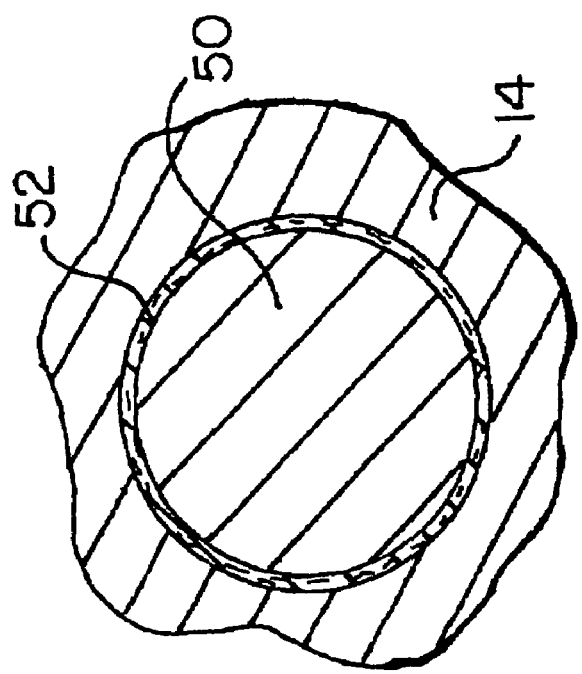
FIGS. 6 and 7 show a cross-sectional schematic view and a top view, respectively, of the implant composition of the present invention used with a surgical implant which has a smooth exterior surface.
Figure 6:
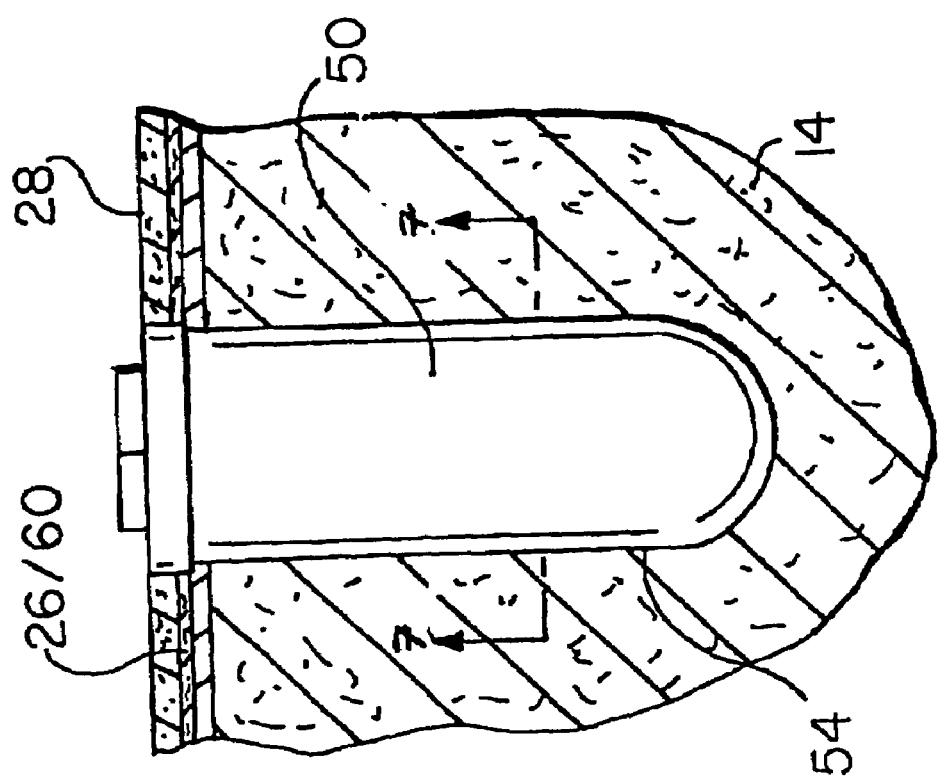

FIG. 5 shows an example of using the implant composition of the present invention with a surgical implant. As shown, a surgical implant 10 is furnished at a surgical site 12 for the purpose of establishing bio-integration with surrounding bone tissue 14. An implant of the type of implant 10 includes buttress treads 16 (or other threading) and an integral collar 18 which comprises an upper part 20 and a lower part 22. Located above bone tissue 14 is a cortical bone layer 24, an optional bio-resorbable barrier layer 26 (described below) and a gum or soft tissue layer 28. The implant composition 30 of the present invention is filled in between bone tissue 14 and surgical implant 10 as an osseo-stimulative. It is to be understood that the implant composition can be applied to implant 10 before insertion into the osseotomy site or can be applied to the site 12, prior to insertion of the implant. Further, any of the surfaces of implant 10 inclusive of parts 20 and 22 of the collar 18 can be provided with cell growth stimulative microgeometry in accordance with U.S. Pat. No. 6,419,491. When a surgical implant exhibits an entirely smooth external geometry, as is the case with an implant 50 in FIG. 6, an osseostimulative surface 52 (FIG. 7) made of the implant composition of the present invention is more suitable when physically adhered to the implant at a pre-operative site. It is, however, to be appreciated that a paste of the implant composition can be applied to an osseotomy site in combination with use of implant 50 and its osseo-stimulative surface 52.

EXAMPLE

In vitro degradation profiles polymer-containing particles according to an embodiment of the present invention having calcium sulfate to PLLA weight ratio of about 96:4 (hereinafter referred to as "BoneGen-TR") and pure calcium sulfate were determined. One-twentieth of a gram of each material was weighed, wrapped in porous nylon mesh, and weighed again to determine the weight of the nylon mesh. It was then incubated in simulated body fluid (SBF) for one hour, removed from SBF, air-dried, and weighed again. This weight was considered the baseline weight to perform future calculations and to determine degradation profiles for each of the materials. Samples were then incubated in the SBF, removed from the fluid every fourth day, air-dried, and weighed. The SBF was then discarded and the test materials were again incubated in fresh SBF. Samples were weighed until three (3) consecutive readings showed no loss of weight.

In vivo studies: BoneGen-TR pellets were sterilized by gamma radiation. The bone response to BoneGen-TR and pure calcium sulfate was studied in a rabbit tibial intramedullary canal model. Twelve New Zealand White rabbits were used in this study. A surgical incision was made over the antero-medial aspect of the proximal tibia below the tibial plateau to gain access to the proximal intramedullary canal. The periosteum was elevated and a 3.0 mm diameter opening was made in the cortex using a 1.0 mm bur bit and 2.0 mm and 3.0 mm spade bits. Each defect was packed with BoneGen-TR or a pure calcium sulfate control (SurgiPlaster), filling the intramedullary canal with 0.3-0.5 ml of the material using a small funnel and delivery system. The site was closed by suturing the periosteum over the bone opening and suturing the subcutaneous, and cutaneous layers with interrupted resorbable sutures. Animals were sacrificed at 4 weeks (5 animals), 8 weeks (5 animals) and 16 weeks (2 animals). Based on previous experience and published literature, pure calcium sulfate (SurgiPlaster) degrades completely by 4-5 weeks and, hence, it was not implanted in animals to be sacrificed at 16 weeks.

Analysis of Specimens: After sacrifice, gross examination of the implant area was performed. The portion of the tibia with the specimens was harvested after sacrifice. These samples were first imaged using a high resolution Faxitron x-ray system. The specimens were then preserved in 70% ethanol and dehydrated in increasing concentrations of ethyl alcohol. Phosphate buffered formalin was not used because the phosphate buffer can cause formation of artifactual mineral deposits. Ethanol adequately preserves the tissue, stops dissolution of the CS component, and preserves mineral structure. They were finally infiltrated and embedded in hard poly (methyl) methacrylate (PMMA).

Micro Computed Tomography analysis (MicroCT): Embedded and unembedded samples were examined using a Scanco 40 microCT system (Scanco Medical, Geneva, Switzerland). Samples were analyzed at 70 kvp, with 150 ms dwell timer and 12 μm resolution. Planar images were used to examine local bone response, degradation of the test materials, and in some cases, to measure volumetric amounts of bone present.

Sectioning of Embedded Specimens: A Buehler Isomet™ low speed saw and Isocut® diamond wafering blade were used to obtain histological sections 300 μthick. These sections were then polished to a 1200 grit finish and examined using both scanning electron microscope (in back scattered electron imaging and x-ray microanalysis modes) and light histopathology.

Backscattered Electron Imaging (BEI) and X-ray Microprobe (XRM) Analysis: BEI (examined under Hitachi S3500N scanning electron microscope) mode provides information about microscopic structure and density of the specimens. This allows visualization of bone formation and remodeling as well as changes in the test materials. XRM (Princeton Gamma Tech IMIX system with PRISM light element detector) was used to analyze changes in the chemical composition of test materials.

Histopathological Analysis: The cut sections were mounted on Plexiglas slides and ground down to 50-80 μthick sections. A Stevenel's Blue and Van Giesons Picro-Fuschin differential tissue staining protocol (SVG) was used for staining the sections. SVG stains soft tissue green-blue, muscle blue-green, cartilage violetblue and mineralized tissue red to orange. The stained sections were also examined microscopically using both transmitted and incident light for any significant tissue response to the implanted test materials. The sections were then photographed at various magnifications using an Olympus SZ10 compound stereomicroscope with attached Olympus microphotography equipment.

Figure 9:
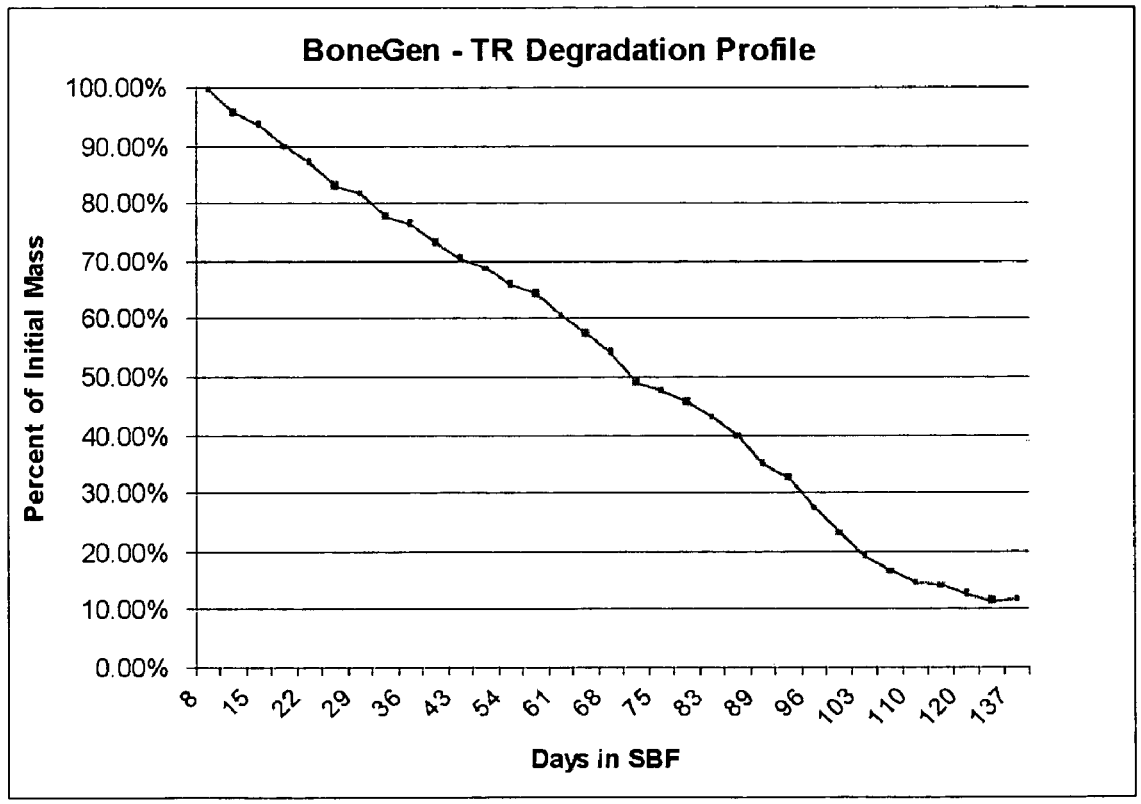
FIG. 9 is a degradation profile of an implant composition material according to one embodiment of the present invention.

Results: In Vitro Degradation of BoneGen-TR: BoneGen-TR underwent slower degradation as compared to pure calcium sulfate. Previous studies of the in vitro degradation of pure calcium sulfate demonstrate complete degradation by the end of 4 or 5 weeks. BoneGen-TR underwent almost linear degradation with a half life of approximately 75 days. See FIG. 9 illustrating the BoneGen-TR degradation profile.

In vivo results: 4 week observations. Pure calcium sulfate implants were completely degraded at the 4-week time point. This material left behind some residual calcium phosphate deposits at this time point and developed very little bone in-growth in this type of animal model. Faxitron x-rays, scanning electron micrographs, and histopathology showed that BoneGen-TR degraded at a significantly slower rate than the pure calcium sulfate and showed little degradation at 4 weeks (FIG. 10A). SEM and corresponding XRM evaluation of BoneGen-TR implants showed that most of the implant was still calcium sulfate. But calcium phosphate was detected at the interface of the BoneGen-TR implant and surrounding bone. Histological analysis showed that osteoblast cells attached to the BoneGen-TR pellets and bone formed around individual BoneGen-TR pellets. Formation of calcium phosphate at the interface of the BoneGen-TR implant and bone and attachment of cells to individual BoneGen-TR pellets are two important early signs of a good bone response to Bone-Gen-TR.

FIG. 10A is a Faxitron image of BoneGen-TR at 4 weeks, illustrating that it has not undergone much degradation at 4 weeks. In contrast, a Faxitron image of pure calcium sulfate implant at 4 weeks, shown in FIG. 10B, illustrates that most of the original pure calcium sulfate implant degraded and hence is not visible. Very little bone formation is observed.

FIG. 11 is a SEM of BoneGen-TR implant at 4 weeks with corresponding XRM. Most of the implant is still calcium sulfate, but calcium phosphate is observed at the interface.

Figure 12A:
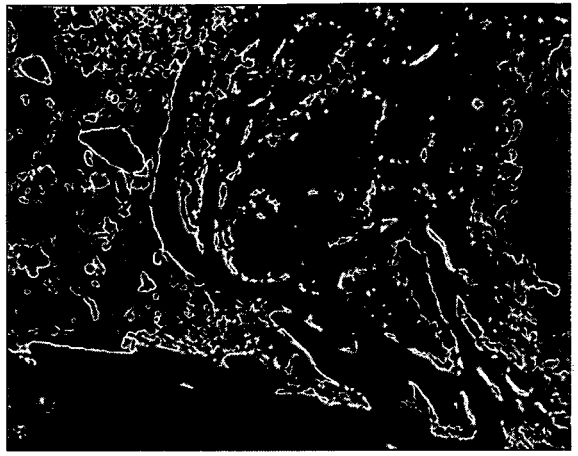
FIG. 12A is an image illustrating the histological response of a bone having an implant composition material according to one embodiment of the present invention at four weeks after implantation.
Figure 12B:
FIG. 12B is an enlarged image illustrating the histological response of the implant composition material according to the embodiment shown in FIG. 12A, illustrating a particle 1202 of the bone composition material, illustrating cells being attached to the particle and bone forming around the particle at four weeks after implantation.

FIGS. 12A-12B illustrate photos of a histological response to BoneGen-TR at 4 weeks. In FIG. 12A, BoneGen-TR pellets are still present, but they are breaking down, with some bone in-growth being apparent. FIG. 12B illustrates a high magnification view illustrating cells attaching to BoneGen-TR and bone forming around individual pellets.

Figure 13A:
FIG. 13A is an image of a bone having an implant composition material according to one embodiment of the present invention after eight weeks from implantation, illustrating bone growth in areas just outside the filler material.

8 week observations. At the end of 8 weeks, BoneGen-TR pellets were seen slowly degrading. Significant quantities of new bone were observed on the surfaces of the BoneGen-TR pellets (see FIG. 13A). Calcium phosphate formation at the periphery of the implant was observed on faxitron images and histological slides. Micro CT showed most of the original defect was filled with mineral. The original BoneGen-TR implant and newly formed calcium phosphate contributed to this mineral. Pure calcium sulfate implants were completely degraded (see FIG. 13B). No trace of original implant was observed at 8 weeks. At the same time, only small amounts of bone were formed in the defects filled with pure calcium sulfate implants. Histological pictures showed that the defects were filled with soft tissue and a minimal amount of bone.

FIG. 14A illustrates histological response to BoneGen-TR pellets at 8 weeks. As shown, bone is present towards the periphery of implant. Most of the BoneGen-TR pellets are still present. Some of the pellets are converting to calcium phosphate and hence pick-up dark stain. FIG. 14B illustrates the histological response to pure calcium sulfate implant at 8 weeks, illustrating dark soft tissue mass with some dark staining mineral; bone is present in only small amounts.

Figure 15A:
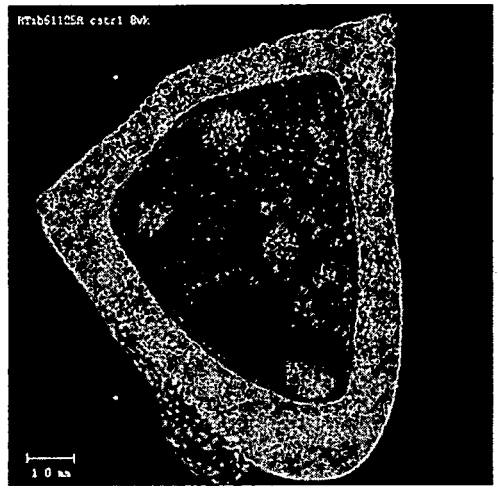
FIG. 15A is a planar X-ray of a bone having an implant composition material according to one embodiment of the present invention at eight weeks after implantation.
Figure 15B:
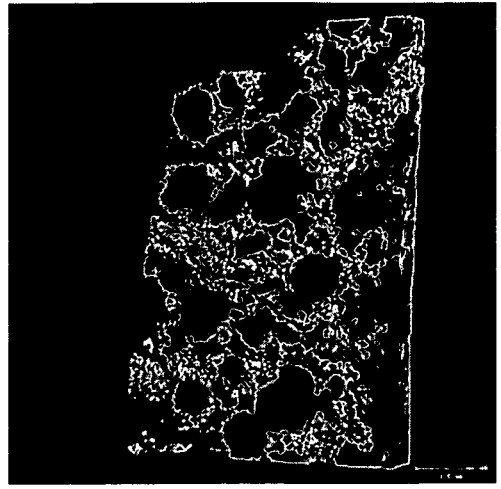
FIG. 15B is a micro CT slice from the bone of FIG. 15A
Figure 15C:
FIG. 15C is a micro CT slice of a bone having an implant composition material comprising pure calcium sulfate implant at eight weeks after implantation.

Planar x-ray and thick slices (FIGS. 15A and 15B) of the BoneGen-TR implants, obtained at 8 weeks using micro CT, showed that most of the defect was filled with mineral deposits, pellets, and bone. Mineral fill was 51.4% (FIG. 15A); however, it is difficult to distinguish BoneGen-TR pellets from new calcium phosphate mineral deposits because they have similar densities. FIG. 15B illustrates a micro CT thick slice from same BoneGen-TR sample as shown in FIG. 15A. It showed 48.6% fill with the same components. FIG. 15C is a micro CT thick slice of a pure calcium sulfate implant at 8 weeks; new bone inside canal with cortex removed. It shows very little bone formation.

Figure 16:
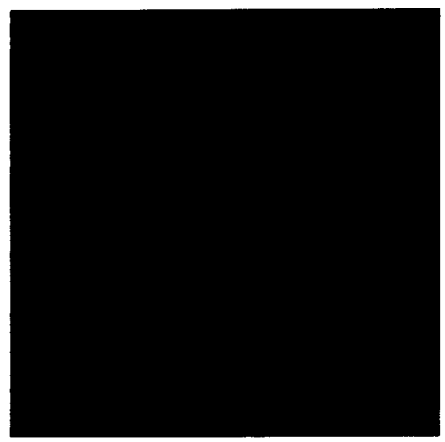
FIG. 16 is an image of a bone having an implant composition material according to one embodiment of the present invention of the present invention at sixteen weeks after implantation.
Figure 17A:
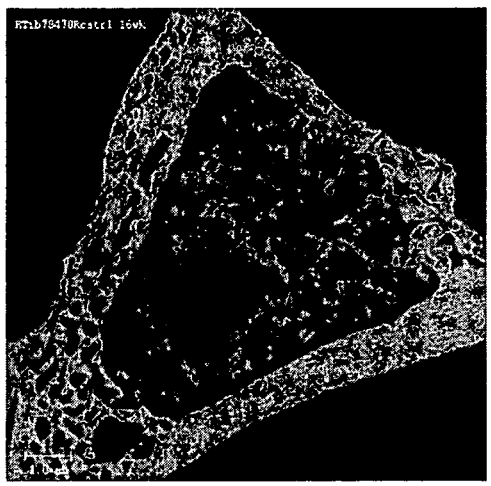
FIG. 17A is a micro CT image of a bone having an implant composition material according to one embodiment of the present invention at sixteen weeks after implantation.
Figure 17B:
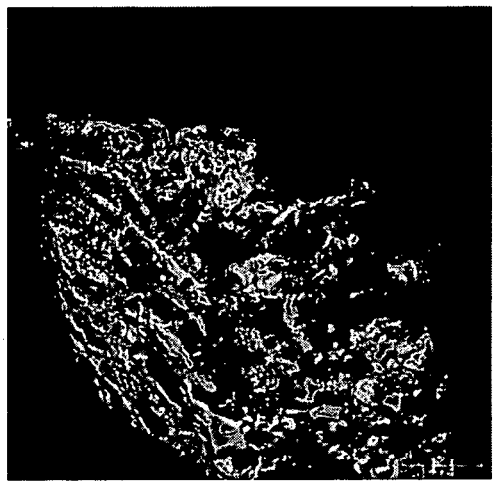
FIG. 17B is an image of a micro CT slice of the same implant shown in FIG. 17A.

16 week observations. The most interesting results were obtained at 16 weeks post implantation. At this time point, most of the BoneGen-TR implant was degraded; it left behind proliferating new bone which was seen on faxitron and micro CT as shown in FIG. 16. Planar x-ray and thick slices (FIGS. 17A-17B) obtained using micro CT showed that most of the mineral deposits observed in defects filled with BoneGen-TR samples at 8 weeks were resorbed and the defects were filled with immature trabecular bone. Bone formation in the defect was measured up to 22%. There is typically very little bone formed in the rabbit intramedullary canal. Considering this fact, the amount of bone observed in the defect is extremely significant. Specifically, as shown in FIG. 17A, mineral fill observed in FIG. 15A has resorbed and is filled with immature trabecular bone; 17.35% of the total area was filled with bone. In FIG. 17B, a micro CT thick slice of the same Bone-Gen-TR sample illustrates new bone inside canal with cortex removed. Bone pattern is sometimes observed in the form of nodules or ghosts of the BoneGen-TR pellets.

Figure 18A:
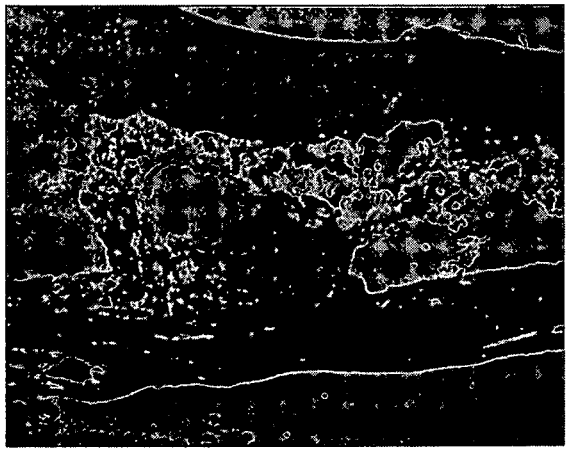
FIG. 18A an image illustrating the histological response of a bone having an implant composition material according to one embodiment of the present invention at 16 weeks after implantation.
Figure 18B:
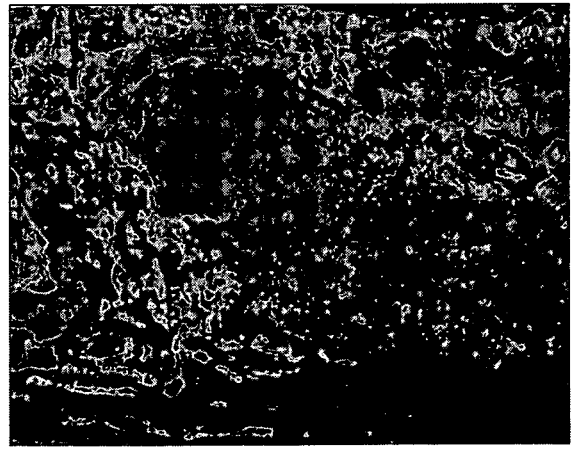
FIG. 18B is an enlarged image of that of FIG. 18A.

These observations were confirmed histologically. The original BoneGen-TR implant was completely degraded and the defect was filled with newly formed bone and calcium phosphate mineral. FIGS. 18A-18B illustrate the histological response to BoneGen-TR at 16 weeks: no BoneGen-TR pellets are observed. The dark staining area is calcium phosphate formed as a result of BoneGen-TR degradation interspersed with bone. Significant amounts of new bone are present. Bone grows from the endosteum towards the center of the medullary canal. In these sections it has not yet reached the center of the canal, but there is significant bone filling.

Conclusions: This study has demonstrated that:
BoneGen-TR is completely degradable in vitro and in vivo.
It is biodegradable and osteoconductive.
It elicits a benign cellular and tissue response at early and late time points.
When implanted in the body, it degrades and facilitates the formation of new bone in the defect.

Whereas pure calcium sulfate implants were completely degraded within 4 weeks and encouraged only small amounts of bone formation, BoneGen-TR implants took 16 weeks to degrade and stimulated vigorous bone formation into the defects without any adverse tissue response. Based on these observations, it can be concluded that BoneGen-TR is a safe and efficacious bone graft material.

The implant materials of the present invention can be sold as a kit. The kit can comprise dry powder of calcium sulfate compound, one or more types of polymer containing particles. The kit can further comprise a setting agent packed in a container. The kit can also include instructions on how to prepare the implant mixture, apply it in a recipient site and set it into the solid implant composition.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

We claim:

1. A method for manufacturing particles for use in forming a resorbable implant for stimulating bone growth, the method comprising: rotating calcium sulfate powder in a drum at a first predetermined drum speed; a first spraying of a resorbable polymer solution at a first predetermined rate on the calcium sulfate powder over a first predetermined period of time; and drying the resulting particles, wherein said resorbable polymer solution comprises a resorbable polymer comprising aliphatic polyester of alpha-hydroxy acid derivatives, poly(desaminotyrosyl-tyrosine alkyl ester carbonate), or therapeutic polymers containing salicylate, and a solvent.

2. The method according to claim 1, wherein the first predetermined drum speed is between about 200 and 400 RPM during spraying.

3. The method according to claim 1, wherein first predetermined drum speed is between about 300 and 400 RPM during spraying.

4. The method according to claim 1, wherein the first predetermined drum speed is about 350 RPM during spraying.

5. The method according to claim 1, wherein the particles comprise about 0.1% to about 22% (w/w) of a resorbable polymer.

6. The method according to claim 1, wherein the first predetermined rate comprises between about 50 and 70 grams per minute.

7. The method according to claim 1, wherein the first predetermined rate comprises about 60 grams per minute.

8. The method according to claim 1, wherein the first predetermined period of time comprises between about 10 to 20 minutes.

9. The method according to claim 1, wherein the first predetermined period of time comprises about 15 minutes.

10. The method according to claim 1, wherein the solvent comprises methylene chloride.

11. The method according to claim 1, wherein the resorbable polymer comprises L-polylactide.

12. The method according to claim 1, wherein a weight ratio of the resorbable polymer to the solvent in the resorbable polymer solution is between about 1:200 and about 1:300.

13. The method according to claim 1, wherein a weight ratio of the resorbable polymer to the solvent in the resorbable polymer solution is about 1:250.

14. The method according to claim 1, further comprising a second spraying the resorbable polymer solution after completing the first spraying.

15. The method according to claim 14, wherein the second spraying is carried out over a second predetermined period of time.

16. The method according to claim 14, wherein the second spraying is carried out at a second predetermined rate.

17. The method according to claim 14, wherein the second spraying is carried out at a second predetermined drum speed.

18. The method according to claim 17, wherein the second predetermined drum speed is faster than the first predetermined drum speed.

19. The method according to claim 17, wherein the second predetermined drum speed is between about 300 to about 500 RPM.

20. The method according to claim 17, wherein the second predetermined drum speed is about 400 RPM.

21. The method according to claim 15, wherein the second predetermined period of time is between about 100 and 300 minutes.

22. The method according to claim 15, wherein the second predetermined period of time is between about 150 and 250 minutes.

23. The method according to claim 16, wherein the second predetermined rate is between about 30 and 50 grams per minute.

24. The method according to claim 16, wherein the second predetermined rate is about 40 grams per minute.

25. The method according to claim 1, wherein said drying comprises spinning the particles in the drum for a further period of time.

26. The method according to claim 25, wherein said further period of time is between about 40 and about 80 minutes.

27. The method according to claim 25, wherein said further period of time is about 60 minutes.

28. The method according to claim 25, wherein the drum is rotated at a further predetermined drum speed.

29. The method according to claim 28, wherein said further predetermined drum speed is between about 100 and about 300 RPM.

30. The method according to claim 28, wherein said further predetermined drum speed is about 250 RPM.

31. The method according to claim 1, wherein the calcium sulfate powder is rotated in the drum at a temperature between about 40° C. and about 80° C.

32. The method according to claim 1, wherein the calcium sulfate powder in rotated is the drum at a temperature about 50° C.

33. The method according to claim 1, wherein said poly (desaminotyrosyl-tyrosine alkyl ester carbonate) comprises poly(desaminotyrosyl-tyrosine ethyl ester carbonates), poly (desaminotyrosyl-tyrosine butyl ester carbonates), poly(desaminotyrosyl-tyrosine hexyl ester carbonates), or poly(desaminotyrosyl-tyrosine octyl ester carbonates).

34. The method according to claim 1, wherein said aliphatic polyester of alpha-hydroxy acid derivatives is a polylactide.

35. The method according to claim 1, wherein said aliphatic polyester of alpha-hydroxy acid derivatives is polyglycolide, polydioxanone, or poly ϵ-caprolactone.

36. A method of manufacturing polymer containing particles as an implant material for stimulating bone growth, comprising:
  (a) rotating powder of a calcium sulfate compound comprising calcium sulfate dihydrate, calcium sulfate hemihydrate or mixture thereof, in a drum at a first predetermined drum speed:
  (b) spraying a resorbable polymer solution with a first predetermined rate on the powder at the first predetermined drum speed over a first predetermined period of time;
  (c) then spraying said resorbable polymer solution on the powder with a second predetermined rate lower than the first predetermined rate at a second predetermined drum speed faster than the first predetermined drum speed over a second predetermined period of time; and
  (d) drying resulting particles.

37. The method according to claim 36, wherein the first predetermined rate comprises between about 50 and 70 grams per minute.

38. The method according to claim 36, wherein the first predetermined drum speed is between about 200 and 400 RPM.

39. The method according to claim 36, wherein the first predetermined period of time comprises between about 10 to 20 minutes.

40. The method according to claim 36, wherein the second predetermined rate is between about 30 and 50 grams per minute.

41. The method according to claim 36, wherein the second predetermined drum speed is about 10% to 20% faster than the first predetermined drum speed.

42. The method according to claim 41, wherein the second predetermined drum speed is between about 300 to about 500 RPM.

43. The method according to claim 36, wherein the second predetermined period of time is between about 100 and 300 minutes.

44. The method according to claim 36, wherein drying comprises spinning the particles in the drum for a third period of time.

45. The method according to claim 44, wherein the third period of time is between about 40 and about 80 minutes.

46. The method according to claim 44, wherein the drum is rotated at a third predetermined drum speed about 25-50% slower than the second predetermined drum speed.

47. The method according to claim 46, wherein the third predetermined drum speed is between about 100 and about 300 RPM.

48. The method according to claim 36, wherein a weight ratio of the resorbable polymer to the solvent in the resorbable polymer solution is between about 1:200 and about 1:300.

49. The method according to claim 36, wherein the solvent comprises methylene chloride.

50. The method according to claim 36, wherein said aliphatic polyester of alpha-hydroxy acid derivatives is a polylactide.

51. The method according to claim 36, wherein said aliphatic polyester of alpha-hydroxy acid derivatives is polyglycolide, polydioxanone, or poly $\epsilon$-caprolactone.

52. The method according to claim 36, wherein said poly (desaminotyrosyl-tyrosine alkyl ester carbonate) comprises poly(desaminotyrosyl-tyrosine ethyl ester carbonates), poly (desaminotyrosyl-tyrosine butyl ester carbonates), poly(desaminotyrosyl-tyrosine hexyl ester carbonates), or poly(desaminotyrosyl-tyrosine octyl ester carbonates).

53. The method according to claim 36, wherein the particles comprise about 0.1% to about 22% (w/w) of a resorbable polymer.

* * * * *